United States Patent [19]

Endo et al.

[11] Patent Number: 4,841,058
[45] Date of Patent: Jun. 20, 1989

[54] VIOLOGEN DERIVATIVE

[75] Inventors: Takeshi Endo; Yoko Nambu; Kazutoshi Yamamoto, all of Yokohama, Japan

[73] Assignee: Asahi Denka Kogyo Kabushiki Kaisha, Tokyo, Japan

[21] Appl. No.: 168,626

[22] Filed: Mar. 7, 1988

Related U.S. Application Data

[63] Continuation of Ser. No. 837,080, Mar. 6, 1986, abandoned.

[51] Int. Cl.$^4$ .............................................. C07D 401/04
[52] U.S. Cl. .................................................... 546/257
[58] Field of Search ......................................... 546/257

[56] References Cited

U.S. PATENT DOCUMENTS 4,089,674  5/1978  Brown et al. ..................... 546/257

FOREIGN PATENT DOCUMENTS 740448  8/1966  Canada ............................... 546/257
56-34496  4/1981  Japan .

Primary Examiner—Jane T. Fan
Attorney, Agent, or Firm—Frishauf, Holtz, Goodman & Woodward

[57] ABSTRACT

The present invention relates to a novel viologen derivative having at least one polymerizable vinyl group directly bonded to a viologen skelton and a process for producing the same.

The novel viologen derivative can be used for a display material, various sensors and the like.

8 Claims, 2 Drawing Sheets

FIG. I

VIOLOGEN DERIVATIVE

This application is a continuation of application Ser. No. 837,080, filed Mar. 6, 1986 now abandoned.

BACKGROUND OF THE INVENTION

1. Field of the Invention

This invention relates to a novel viologen derivative and a process for producing the same. Particularly it relates to a novel viologen derivative having at least one polymerizable vinyl group directly bonded to a viologen skeleton and a process for producing the same.

2. Description of the Prior Art

A viologen derivative easily conducts a reversible oxidation-reduction (redox) reaction under various conditions. It has attracted an attention because the reductant thereof is colored. It has been proposed to be used as photo- or electrochromic display materials, photoelectrochemical cell materials, mediators for redox reactions, various sensors and the like. For this reason, various derivatives and oligomers have been produced so far. Among them, a low molecular viologen derivative has disadvantages such as a short repetition life as well as a slow response and a short memory life when used as an display material. Further a short absorption wavelength has been pointed out as a drawback when used as a photochromic material or the like.

As a countermeasure for avoiding these drawbacks, it has been proposed to use various oligomers and polymers having a viologen group, which are divided roughly into those having a viologen group in a main chain (backbone) and those having a viologen group in a side chain (pendant). However although having a slightly increased stability in redox cycles the formers have disadvantages that an electron transfer rate is considerably lowered and, when used as a film, sufficient film properties are not obtainable. The latters have drawbacks that a stability is lowered, although it has an increased electron transfer rate.

On the other hand, a viologen monomer having a vinyl group has attracted an attention, because it is polymerized and can be modified in various manners. However the monomers which have been proposed until now have a spacer between a vinyl group and a viologen structure, and therefore they could not solve the above mentioned drawbacks.

Accordingly, an object of the present invention is to provide a novel viologen derivative which solve the above mentioned drawbacks and a process for producing the same.

SUMMARY OF THE INVENTION

The above mentioned object of the present invention has been achieved by a vinyl viologen derivative represented by the general formula:

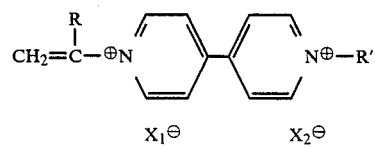
(I)

(wherein R is a hydrogen atom or an aliphatic group having a carbon number of 1 to 6; R' is a member selected from the group consisting of a hydrogen atom, an aliphatic group and an aromatic group; and $X_1^\ominus$ and $X_2^\ominus$ are anions which may be same or different.) As well as a process for producing a vinyl viologen derivative represented by the general formula (I) illustrated above which comprises dehydrohalogenation of a compound represented by the general formula with a base:

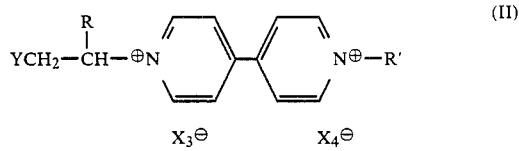
(II)

(wherein R and R' are as mentioned above. $X_3^\ominus$ and $X_4^\ominus$ are anions which may be same or different, and Y is a halogen atom.)

DESCRIPTION OF THE PREFERRED EMBODIMENTS

Figure 1:
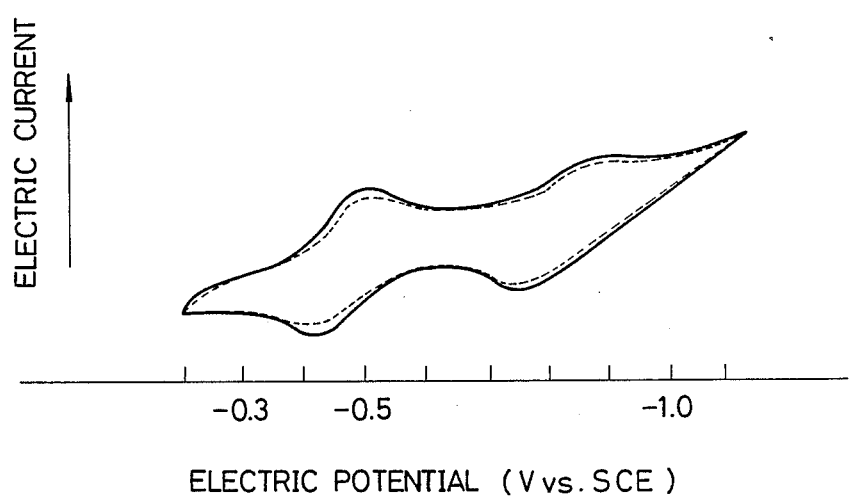
FIG. 1 is a redox wave obtained by cyclic voltammometry of a viologen copolymer film-coated gold electrode prepared in Reference Example 3.

A novel viologen derivative of the present invention is represented by the following general formula (I).

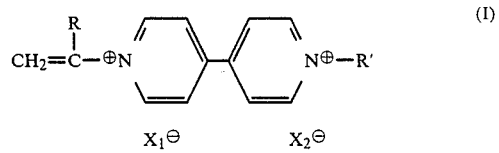
(I)

In the formula, R represents a hydrogen atom or an aliphatic group having a carbon number of 1 to 6. As said aliphatic group, there are exemplified an ordinary aliphatic group as well as an aliphatic group which contains one or more hetero atoms in its main chain and an aliphatic group which is substituted with one or more monovalent group. The examples thereof include, for example, (a) an alkyl or alkenyl group; (b) an aliphatic group in which one valency of a divalent group such as —O—, —S—, —CO—, —SO—, —SO₂—, —COO—, —NH—, or the like is attached to the above mentioned alkyl or alkenyl group (a): (c) an alkyl or alkenyl group which is substituted with a monovalent group such as the aliphatic group (b), halogen, —OH, —COOH or the like. Preferred is an alkyl group such as —CH₃, —C₂H₅, —C₃H₇ and —C₄H₉, and an aliphatic group having one or more hetero atoms in its main chain such as —S—CH₃, —O—C₂H₅, —COO CH₃, —OCO CH₃, —C₂H₄—O—CH₃ and —CH₂OCO CH₃.

R' represents a hydrogen atom, an aliphatic group or an aromatic group. Said aliphatic and aromatic groups include ordinary aliphatic and aromatic groups as well as those having one or more hetero atoms in their main chain and those substituted with one or more monovalent group. As the examples thereof are listed ordinary aliphatic and aromatic group such as alkyl, alkenyl, phenyl, alkyl substituted phenyl, tolyl, naphthyl, anthryl, benzyl, cycloalkyl and cycloalkenyl groups. The aliphatic and aromatic groups may be substituted with (A) a group in which one valency of a divalent group such as —O—, —S—, —CO—, —SO—, —SO₂—, —C O O—, —NH— or the like is attached to the above mentioned ordinary aliphatic or aromatic group of (B) a monovalent group such as halogen, —OH, —COOH, —SH, —NO$_2$ or the like. Preferred are an alkyl group such as —CH$_3$, —C$_2$H$_5$, —C$_3$H$_7$ and —C$_4$H$_9$, an alkenyl group such as —CH=CH$_2$ and —C(R)=CH$_2$, phenyl group, benzyl group, tolyl group, an aliphatic or aromatic group having one or more hetero atoms in its main chain such as —CH$_2$ COCH$_3$, —C$_2$H$_4$OC$_2$H$_5$, —C$_2$H$_4$SCH$_3$, —C$_6$H$_4$—COOCH$_3$, cyclohexyl group, or the like.

$X_1\ominus$ and $X_2\ominus$ may be any anions which can form a stable salt with dipyridium. The stable anion includes a halogen ion (Cl$\ominus$, Br$\ominus$, I$\ominus$), CH$_3$CO$_2\ominus$, HSO$_4\ominus$, CF$_3$CO$_2\ominus$, FSO$_3\ominus$, CH$_3$SO$_3\ominus$, BF$_4\ominus$, PF$_6\ominus$, ClO$_4\ominus$, AsF$_6\ominus$, SbF$_6\ominus$ and so on. An anion supported in a polymer may be included.

As the examples of a novel viologen derivative of the present invention represented by the above mentioned general formula (I), there are exemplified the compounds having the following structures.

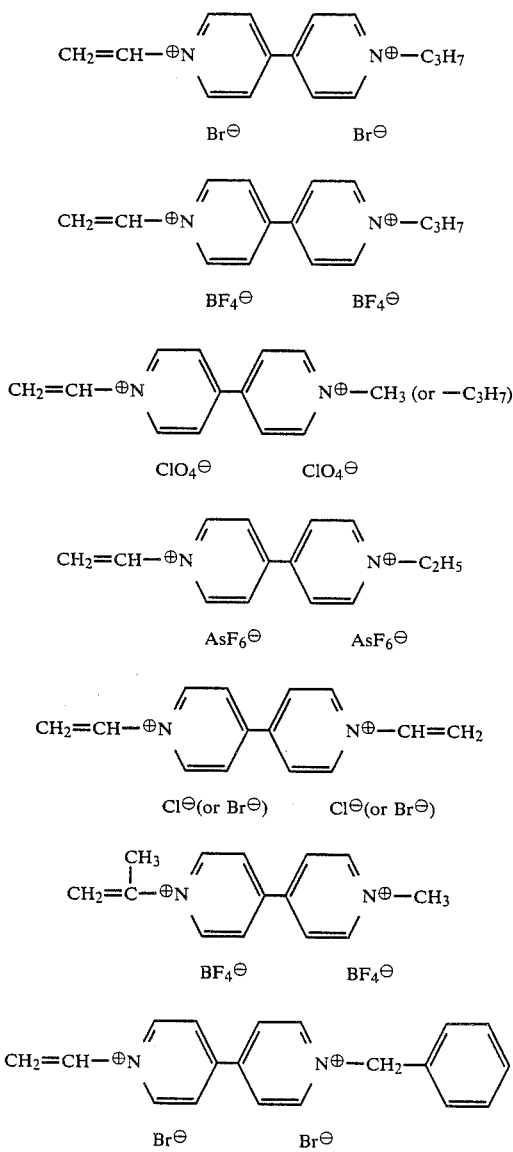

A novel viologen derivative of the present invention represented by the above mentioned general formula (I) can be produced by dehydrohalogenation of a compound represented by the general formula (II) with a base.

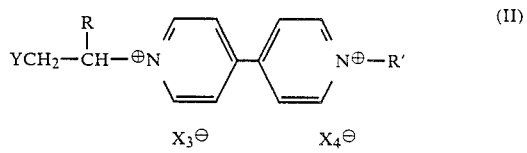

In the formula, R and R' are the same as those defined in the above mentioned general formula (I). Y is a halogen atom (Cl$\ominus$, Br$\ominus$, I$\ominus$). $X_3\ominus$ and $X_4\ominus$ are anions which may be same or different. The anions $X_1\ominus$ and $X_2\ominus$ defined in the above mentioned general formula (I) can be used $X_3\ominus$ and $X_4\ominus$.

The compound represented by the above mentioned general formula (II) can be obtained in high yield by the reaction of a corresponding halogenated hydrocarbon derivative and a dipyridyl derivative, the examples of the reaction being shown below with the chemical equations (III) and (IV).

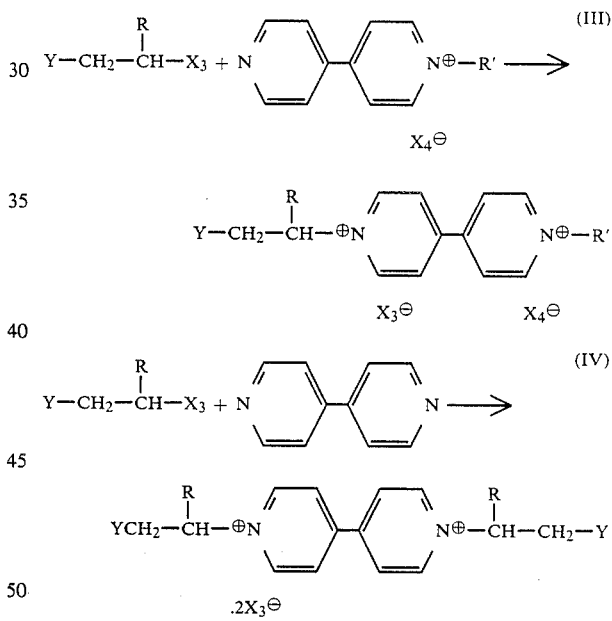

As the base for dehydrohalogenation in the process of the present invention there is used a reagent which is capable of conducting an ordinary dehydrohalogenation reaction. Since the compound represented by the above mentioned general formula (II) is sensitive to dehydrohalogenation, there is also used a base with a weak basicity. The examples of the base used are an inorganic base such as NaOH, KOH and LiOH and an ordinary base such as amines, amine-anions and alkoxides.

The dehydrohalogenation reaction proceeds under mild conditions without heating. Depending on the kinds of the base used, decomposition of a viologen structure may occur as the dehydrohalogenation proceeds. The reaction should be conducted at a temperature as low as possible, for example, from 0 to −50° C.

as long as the time permits. As the solvent for the dehydrohalogenation, there is used a polar solvent such as alcohols and water.

Having at least one vinyl group, the novel viologen derivative of the present invention can be utilized as a monomer for polymerization. The viologen derivative as monomer can be homopolymerized or copolymerized together with another copolymerizable monomer using an ordinary radical initiator.

Further it is useful as monomer for plasma polymerization, radiation polymerization and the like.

As the copolymerizable monomer, there are exemplified the following monomers.

monoolefines such as ethylene, propylene, isobutylene, pentene, hexene -1, 4 - methylpentene-1, butene - 1;

diolefines such as butadiene, 2 - methyl - 1, 3-butadiene, 1, 4 - hexadiene, 2, 3 - dimethyl - 1, 3-butadiene;

halogenated olefines and halogenated diolefines such as vinyl chloride, vinyl fluoride, vinylidene chloride, vinyl bromide, trichloroethylene, tetrafluoroethylene, chlorotrifluoroethylene, vinylidene fluoride, hexafluoropropylene, choloroprene, 2, 3-dichloro - 1, 3 - butadiene;

unsaturated alcohols such as vinyl alcohol and allyl alcohol;

unsaturated ethers such as methyl vinyl ether, isobutyl vinyl ether, isopropyl vinyl ether and other alkyl vinyl ethers as well as alkyl allyl ethers, alkyl (meth)acryl ether, and polyoxyalkylene glycol (meth)allyl ether;

unsaturated aldehydes and unsaturated ketones such as acrolein, methacrolein, croton aldehyde and methyl vinyl ketone;

vinyl esters such as vinyl acetate, vinyl propionate, versatic acid vinyl ester, vinyl chloroacetate and vinyl cinnamate;

allyl esters such as diallyl orthophthalate, diallyl isophthalate, diallyl - 2, 6 - naphtalene dicarboxylate;

unsaturated nitriles such as acrylonitrile and methacrylonitrile;

unsaturated caboxylic acids such as acrylic acid, methacrylic acid, crotonic acid, maleic acid, maleic anhydride and itaconic acid;

unsaturated carboxylic acid esters such as alkyl acrylate, alkyl methacrylate, alkyl maleate and alkyl itaconate;

unsaturated amides such as acrylamide, N, N-dimethylacrylamide, N - alkylol acrylamide and methacrylamide;

cyclic compounds having C=C double bond(s) such as styrene, α - methyl styrene, divinyl benzene, oxystyrene, vinyl benzyl chloride, p - hydroxystyrene, N - vinyl carbazole, 1 - vinyl - 2 - methyl - imidazole, N - vinyl imidazole, 2 - vinyl imidazoline, N - vinyl caprolactam, acryloyl morpholine, N - vinyl pyrrolidone, vinyl pyridine, cinnamoyl methyl styrene, acryloyl morpholine, dialkyl aminomethyl - p - hydro xystyrene, vinyl benzyl trialkyl ammonium chloride, p - vinyl benzene sulfonate; and other monomers such as vinyl isocyanate, vinyl urethane, vinyl sulfonic acid, methoxymethyl vinyl sulfide, vinyl - N, N - dialkyl dithio carbamate and divinyl sulfone.

The following examples further explain the effectiveness of the present invention in a concrete form. However the present invention is not limited to these examples and includes other embodiments which do not depart from the essence of the present invention.

EXAMPLE 1

Synthesis of 1 - propyl - 1' - vinyl - 4, 4'-dipyridinium dibromide.

(1) 1 - propyl - 1' - bromoethyl - 4, 4'-dipyridinium dibromide.

1, 2 - Dibromoethane in an amount of 15.4 ml (0.18 mole) was dissolved in 25 ml of dimethyl formamide and the mixture was heated to 100° C. To the mixture was slowly added dropwise 75 ml of a solution of 5 g (0.018 mole) of 1 - propyl - 4 - (4 - pyridyl)pyridinium bromide in dimethyformamide and the resulting mixture was further stirred at 100° C. for 24 hours. An orange-colored crystal separated was collected by filtration and washed with hot ether. The crystal was recrystallized from 99% ethanol to obtain 6.9 g of a yellowish crystalline powder, 1 - propyl - 1' - bromoethyl 4, 4' - dipyridinium dibromide having the following results of analysis.

(Results of Analysis)

* m.p. 223.5°–224.5° C.
* I.R. $\gamma KBr:_{max}$ 3000, 1638, 1560, 1508, 1455, 1380, 1345, 1265, 1235, 1220, 1195, 1170, 940, 890, 860, 830, 715, 550, 490 cm$^{-1}$.
* N.M.R. ($D_2O$) Internal standard: sodium 2, 2 - dimethyl - 2 - silapentane-5- sulfonate.

δ: 1.0 (3H, t), 2.3 (2H, q), 4.1 (2H, t), 4.6 (2H, t), 5.2 (2H, t), 8.6 (4H, m), 9.2 (4H, m).

* Elementaly Analysis as $C_{15}H_{19}N_2Br_3$

|  | C | H | N |
| --- | --- | --- | --- |
| Calculated (%) | 38.58 | 4.10 | 6.00 |
| Found (%) | 38.58 | 3.98 | 5.97 |

(2) 1 - Propyl - 1' - vinyl - 4, 4' - dipyridinium dibromide

Four grams (0.009 mole) of 1 - propyl - 1' - bromoethyl - 4, 4' - dipyridinium dibromide obtained in (1) above was dissolved in 40 ml of a mixed solvent of methanol and water (3:1). After the mixture was chilled to −10° C., 0.86 ml (0.009 mole) of 10N sodium hydroxide aqueous solution was slowly added dropwise while maintaining the temperature at −10° C. to −15° C., and the resulting mixture was further stirred for 70 minutes. After the reaction, the pH was adjusted to 4 with 48% hydrobromic acid and the solvent was distilled off under reduced pressure to obtain a yellowish powder. The powder was recrystallized from 99% ethanol to obtain 2.5 g of a yellowish cristalline powder, 1-propyl - 1' - vinyl - 4, 4' - dipyridinium dibromide having the following results of analysis.

(Results of Analysis)

* m.p. 203°–204° C.
* I.R. $\gamma KBr:_{max}$ 2980, 1640, 1625, 1550, 1510, 1450, 1420, 1360, 1265, 1255, 1230, 1200, 1175, 1110, 965, 940, 850, 830, 795, 755, 725, 480 cm$^{-1}$.
* N.M.R. ($CD_3OD$) Internal standard: tetramethyl silane δ: 1.1 (2H, t), 2.2 (2H, m), 4.8 (2H, t), 6.1 (1H, m), 6.5 (1H, dd), 7.9 (1H, q), 8.9 (4H, m), 9.5 (4H, m).

* U.V. ($H_2O$) λmax: 270 nm

EXAMPLE 2

Synthesis of 1, 1' - divinyl - 4, 4' - dipyridinium dibromide (1) 1, 1' - Dibromoethyl - 4, 4' - dipyridinium dibromide 1, 2 - Dibromoethane in an amount of 41.3 ml (0.48 mole) was dissolved in 18 ml of dimethylformamide. After the mixture is heated to 100° C., 55 ml of a solution of 2 g (0.013 mole) of 4, 4' - dipyridine in dimethylformamide is slowly added dropwise and the whole mixture was further stirred for 24 hours. A yellowish precipitate deposited was collected by filtration and washed with hot ether. The precipitate was recrystalized from 99% ethanol to obtain 1.6 g of a yellowish crystalline powder, 1, 1' - dibromoethyl - 4, 4' - dipyridinium dibromide having the following results of analysis.

(Results of Analysis)

* m.p. 245°–247° C. * I.R. $\gamma KBr_{max}$ 3000, 1635, 1555, 1510, 1450, 1365, 1305, 1255, 1230, 1195, 1170, 830, 805, 770, 740, 720, 675, 555, 495 cm$^{-1}$.
* N.M.R. (D$_2$O) Internal standard: sodium 2, 2' - dimethyl - 2 - silapentane -5- sulfonate δ: 4.2 (4H, t), 5.3 (4H, t), 8.6 (4H, m), 9.2 (4H, m).
* Elementaly Analysis

|  | C | H | N |
| --- | --- | --- | --- |
| Calculated (%) | 31.61 | 3.03 | 5.27 |
| Found (%) | 31.50 | 2.81 | 5.16 |

(2) 1, 1' - Divinyl - 4, 4' - dipyridinium dibromide 1, 1' - Dibromoethyl - 4, 4' - dipyridinium dibromide (obtained in (1) above) in an amount of 1.6 g (0.002 mole) was dissolved in 20 ml of a mixed solvent of methanol and water (3:1). After the mixture was chilled to −10° C., 0.1 ml (0.001 mole) of 10N sodium hydroxide aqueous solution was slowly added dropwise while maintaining the temperature at −10° C. to −15° C., and the whole mixture was further stirred for 70 minutes. After the reaction, the pH was adjusted to 4 with 48% hydrobromic acid and the solvent was distilled off under reduced pressure to obtain a yellowish powder, which was added into 100 ml of 99% ethanol and heated to 50° C. The remaining solid was recovered by filtration and recrystallized from 99% ethanol to obtain 0.7 g of a yellowish crystalline powder, 1, 1'-divinyl - 4, 4' - dipyridinium dibromide having the following results of analysis.

(Results of Analysis)

* m.p. 244°–246° C.
* I.R. $\gamma KBr_{max}$ 2980, 1640, 1630, 1550, 1510, 1450, 1420, 1360, 1265, 1255, 1230, 1200, 1175, 1110, 965, 940, 845, 830, 795, 755, 725, 480 cm$^{-1}$.
* N.M.R. (D$_2$O) Internal standard: sodium 2, 2' - dimethyl - 2 - silapentane -5- sulfonate.

δ: 6.1 (4H, d), 6.4 (2H, dd), 7.7 (2H, dd), 8.8 (4H, m), 9.3 (4H, m).
* U.V. $\gamma$max: 290 nm.

EXAMPLE 3

Synthesis of 1 - propyl - 1' - vinyl - 4, 4'-dipyridinium diperchlorate

1 - Propyl - 1' - vinyl - 4, 4' - dipyridinium dibromide (Synthesized in Example 1) in an amount of 2.0 g (0.005 mole) was dissolved in 50 ml of methanol. 5 ml of 60% perchloric acid was added dropwise and a Chinese yellowish precipitate separated was collected by filtration and recrystallized from ethanol to obtain 1.2 g of 1 - propyl - 1' - vinyl 4, 4' - dipyridinium diperchlorate having the following results of analysis.

(Results of Analysis)

* m.p. 228.5°–229.5° C.
* I.R. $\gamma KBr_{max}$ 3020, 1645, 1630, 1560, 1510, 1450, 1415, 1360, 1305, 1260, 1230, 1200, 1000,–1180, 950, 845, 835, 810, 750, 725, 580, 530, 520, 480 cm$^{-1}$.
* Elementaly Analysis as $C_{15}H_{18}N_2Cl_2O_8$

|  | C | H | N |
| --- | --- | --- | --- |
| Calculated (%) | 42.37 | 4.27 | 6.59 |
| Found (%) | 42.02 | 4.21 | 6.76 |

EXAMPLE 4

Synthesis of 1 - propyl - 1' - vinyl - 4, 4'-dipyridinium difluoroborate

1 - Propyl - 1' - vinyl - 4, 4' - dipyridinium dibromide (synthesized in Example 1) is an amount of 2.5 g (0.006 mole) was dissolved in 100 ml of methanol, to which was added dropwise 100 ml of a methanolic solution of 2.5 g (0.013 mole) of silver borofluoride and the resulting white precipitate of silver bromide was filtered off. The filtrate was partially condensed and cooled to obtain a Chinese yellowish cristalline powder. The powder was recrystallized from 99% ethanol to obtain 1.2 g of 1 - propyl - 1' - vinyl 4, 4'-dipyridinium difluoroborate having the following results of analysis.

(Results of Analysis)

* m.p. 228.5°–229.5° C.
* I.R. $\gamma KBr_{max}$ 3010, 1645, 1635, 1560, 1510, 1450, 1415, 1360, 1305, 1260, 1230, 1200, 1020–1170, 950, 845, 835, 810, 750, 725, 580, 530, 520, 480 cm$^{-1}$.

REFERENCE EXAMPLE 1

Synthesis of a copolymer of 1 - propyl - 1' - vinyl - 4, 4' - dipyridinium salt and acrylonitrile Pyrex polymerization tubes were charged with a weighed amount (0.2–1.2 milimoles) of 1 - propyl - 1' - vinyl 4, 4' - dipyridinium diperchlorate obtained in Example 3 or 1 - propyl - 1' - vinyl 4, 4' - dipyridinium fluoroborate obtained in Example 4 and a weighed amount (2.4–3.8 milimoles) of acrylonitrile, to each of which was added 1 ml of γ - butyrolactone to make a solution. After adding azobisisobutyronitrile (1 mole %) to the solution and replacing the air with nitrogen, the tube was evacuated and sealed and thereafter heated at 80° C. for 16 hours. The reaction mixture was dropped into methanol to form a precipitate, which was collected by filtration. The recovered precipitate was dried under reduced pressure and thereafter dissolved in dimethylformamide to form a solution. The solution was dropped into methanol to obtain a Chinese yellowish powder of a copolymer of 1 - propyl - 1' - vinyl - 4, 4' - dipyridinium diperchlorate and acrylonitrile or a copolymer of 1 - propyl - 1' - vinyl - 4, 4'-dipyridinium fluoroborate and acrylonitrile. The results of analysis of these copolymers are shown below.

* I.R. $\gamma KBr_{max}$ 3650, 3350, 2930, 2250, 1640, 1450, 1340,–1390, 1150, 1120, 1080, 825, 620, 520 cm$^{-1}$.
* I.R. (copolymer with the fluoroborate) $\gamma$: 3700–3500, 3000, 2250, 1640, 1455, 1380, 1350, 1270, 1180, 1040–1100, 850, 825 cm$^{-1}$.

N. M. R. ( $(CD_3)_2SO$) Internal Standard: tetramethyl silane

δ: 1.0 (t), 2.1, 3.2, 4.3, 4.7, 8.9, 9.6

From the results of the elementaly analysis and N. M. R. of the copolymers, the molar ratios of the viologen moiety and the acrylonitrile moiety in the copolymers were calculated. The results of calculation were shown in Table 1 together with the yield.

TABLE 1

| Molar ration of viologen monomer: acrylonitrile monomer | Yield (%) | Molar ratio of viologen moiety: acrylonitrile moiety in the copolymer |
|---|---|---|
| 5:95[1] | 43.5 | 6:94 |
| 30:70[1] | 23.0 | 30:70 |
| 5:95[2] | 73.0 | 6:94 |

[1]perchlorate
[2]fluoroborate

REFERENCE EXAMPLE 2

Cyclic voltammometry of the viologen derivatives

The viologen derivatives synthesized in Examples 1 and 2, 1 - propyl - 1' - vinyl - 4, 4' - dipyridinium dibromide and 1, 1' - divinyl 4, 4' - dipyridinium dibromide were each dissolved in 0.1M - tris buffer solution (pH 8.0)–0.2M potassium chloride solution to prepare 1 milimolar solution of the viologen derivative. The cyclic voltammogram of the viologen derivative was measured using a saturated calomel electrode as a reference electrode and platinum as working electrode and counter electrode. Each case shows a two redox wave based on oxidation-reduction process between an one-electron reductant and a two-electron reductant of the viologen. The redox potential obtained is shown in Table 2 below.

TABLE 2

| viologen derivative | (1) $E_I \frac{1}{2} E_{II} \frac{1}{2}$ (volt) | (2) (volt) |
|---|---|---|
| monovinyl derivative | −0.53 | −0.71 |
| divinyl derivative | −0.47 | −0.93 |

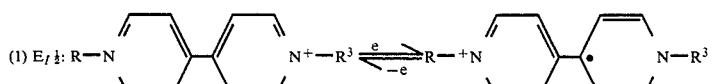
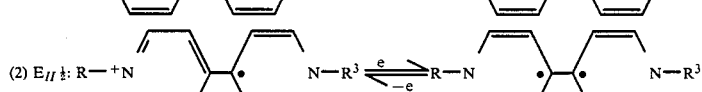

REFERENCE EXAMPLE 3

Preparation of a viologen copolymer film-coated electrode and its cyclic voltammometry Ten miligrams of the copolymer of 1 - propyl - 1'- vinyl 4, 4' - dipyridinium diperchlorate and acrylonitrile (molar ratio of the diperchlorate monomer and acrylnitrile monomer being 1:19) synthesized in Reference Example 1 was dissolved in 0.5 ml of dimethylformamide to form a solution, which was casted on a gold electrode (diameter 0.4 cm) the periphery of which was insulated with teflon. The solvent was removed by heating at 60° C. whereby a viologen copolymer film-coated gold electrode was obtained. The cyclic voltammogram in pH 8-0.2M potassium chloride solution was measured using the gold electrode as working electrode and platinum as counter electrode. As the results, a two step redox wave (shown in FIG. 1) was obtained (scanning rate: $2 \times 10^2$ mV/sec). In FIG. 1, the solid line shows a redox wave in the first time of use and the dotted line shows a redox wave in the 10th time of use.

COMPARATIVE EXAMPLE

In the same manner as in Reference Example 3, there was prepared an electrode which was coated with a polymer film of a copolymer of 1 - methyl - 1' - p -vinylbenzyl - 4, 4' - dipyridinium salt and acrylonitrile.

Figure 2:
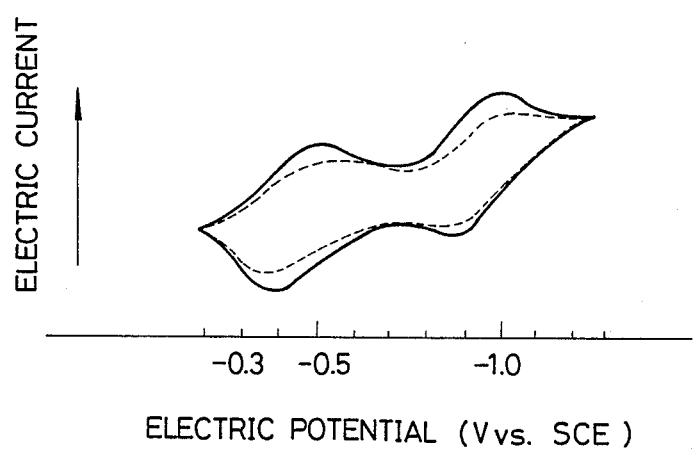
FIG. 2 is a redox wave of a polymer film-coated electrode prepared in Comparative Example.

The results of its cyclic voltammogram measurement are shown in FIG. 2 (scanning rate: $2 \times 10^2$ mV/sec). In FIG. 2, the solid line shows a redox wave in the first time of use and the dotted line shows a redox wave in the third time of use.

The viologen derivative of the present invention can be used for photo- or electrochromic display indicating materials, photoelectric cell materials, mediators for oxidation-reduction reactions, various sensors or the like. The compound represented by the general formula (I) particularly shows an U.V. absorption of high wavelength and a low redox potential both of which have not been realized in the conventional viologen derivatives. Further the copolymer obtained from the novel viologen derivative of the present invention shows a remarkably increased stability (and a resistance) to the repeated use with an oxidation-reduction reaction, which stability (resistance) could not be realized in the conventional oligomers and polymers.

What is claimed is:

1. A vinyl viologen derivative represented by the formula:

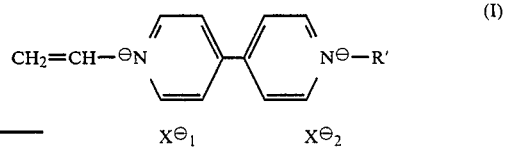

wherein

R' is a hydrogen atom; tolyl; benzyl a $C_1$–$C_6$ alkyl; a $C_2$–$C_6$ alkenyl; a $C_3$–$C_6$ cycloaklyl; a $C_6$–$C_{10}$ unsubstituted aromatic group; substituted $C_1$–$C_6$ alkyl, substituted $C_2$–$C_6$ alkenyl or substituted $C_6$–$C_{10}$ aromatic, wherein the substituent is —OH; and $X_1$ and $X_2$ are anions which may be same or different.

2. A vinyl viologen derivative of claim 1, wherein $X_1$ and $X_2$ are anions which form a stable salt with bipyridinium.

3. A vinyl viologen derivative designated:

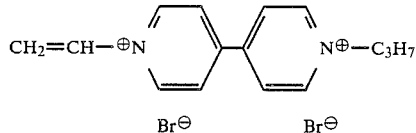

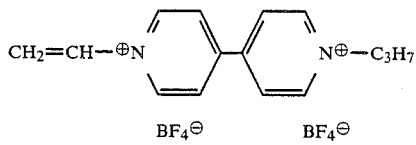

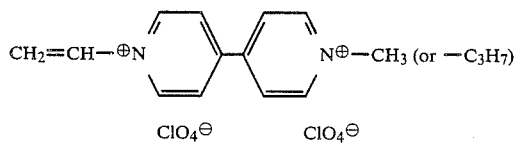

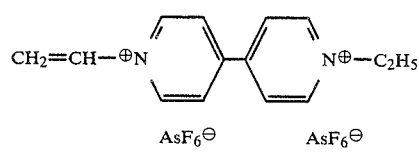

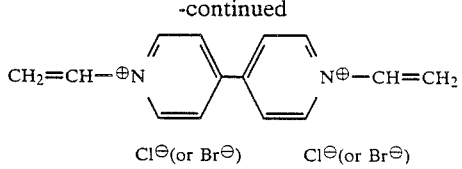

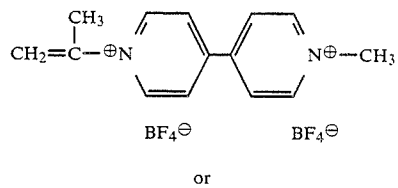

or

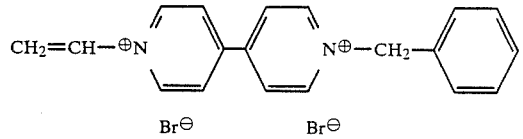

4. The vinyl viologen derivative of claim 1 wherein R' is —$CH_3$, —$C_2H_5$, —$C_3H_7$, $C_4H_9$, —$CH=CH_2$, phenyl, benzyl, tolyl, or cyclohexyl.

5. The vinyl viologen derivative of claim 1 wherein $X_1$ and $X_2$ are each selected from the group consisting of $Cl^-$, $Br^-$, $I^-$, $CH_3CO_2^-$, $HSO_4^-$, $CF_3CO_2^-$, $FSO_3^-$, $CH_3SO_3^-$, $BF_4^-$, $PF_6^-$, $ClO_4^-$, $AsF_6^-$ or $SbF_6^-$.

6. The vinyl viologen derivative of claim 10 wherein R' is —$CH_3$, —$C_2H_5$, —$C_3H_7$, $C_4H_9$, —$CH=CH_2$, phenyl, benzyl, tolyl, or cyclohexyl.

7. The vinyl viologen derivative of claim 1 designated 1-propyl-1'-vinyl-4,4'-dipyridinium dibromide.

8. The vinyl viologen derivative of claim 1 designated 1-propyl-1'-vinyl-4,4'-dipyridinium diperchlorate.

* * * * *